US010561822B2

(12) United States Patent
  Wang

(10) Patent No.: US 10,561,822 B2
(45) Date of Patent: Feb. 18, 2020

(54) TRACHEOSCOPE

(71) Applicant: Zhuhai Kaden Medical Imaging Technology Co., Ltd, Zhuhai, Guangdong (CN)

(72) Inventor: Nanbing Wang, Guangdong (CN)

(73) Assignee: Zhuhai Kaden Medical Imaging Technology Co., Ltd, Zhuhai (CN)

( * ) Notice: Subject to any disclaimer, the term of this patent is extended or adjusted under 35 U.S.C. 154(b) by 171 days.

(21) Appl. No.: 15/879,472

(22) Filed: Jan. 25, 2018

(65) Prior Publication Data
  US 2018/0207403 A1    Jul. 26, 2018

(30) Foreign Application Priority Data

Jan. 25, 2017  (TW) .............................. 106102871 A
Jan. 25, 2017  (TW) .............................. 106201408 U

(51) Int. Cl.
  *A61M 25/01*   (2006.01)
  *A61M 25/00*   (2006.01)
  *A61B 1/00*    (2006.01)
  *A61B 1/005*   (2006.01)
  *A61B 1/267*   (2006.01)
  *A61M 16/04*   (2006.01)
  *A61B 1/06*    (2006.01)

(52) U.S. Cl.
  CPC ..... *A61M 25/0147* (2013.01); *A61B 1/00039* (2013.01); *A61B 1/0052* (2013.01); *A61B 1/0057* (2013.01); *A61B 1/267* (2013.01); *A61M 16/0472* (2013.01); *A61M 25/00* (2013.01); *A61M 25/01* (2013.01); *A61M 25/0136* (2013.01); *A61B 1/0055* (2013.01); *A61B 1/0676* (2013.01)

(58) Field of Classification Search
  CPC .. A61M 25/01; A61M 25/0147; A61M 25/04; A61M 25/0472; A61B 1/00; A61B 1/005; A61B 1/0052
  See application file for complete search history.

(56) References Cited

U.S. PATENT DOCUMENTS

| 7,681,576 | B2 * | 3/2010 | Thomas | A61M 16/04 128/207.14 |
| 8,573,218 | B2 * | 11/2013 | Rutter | A61M 16/0465 128/200.24 |
| 8,887,730 | B2 * | 11/2014 | Wood | A61M 16/0434 128/207.14 |
| 9,155,856 | B2 * | 10/2015 | Munaro | A61M 16/0472 |
| 9,398,837 | B2 * | 7/2016 | Vazales | A61B 1/0669 |

(Continued)

*Primary Examiner* — Christopher J Beccia

(57) ABSTRACT

A tracheoscope includes a handle having a control mechanism; one end of the handle is connected with a plug-in type screen, and the other end of the handle is combined with a catheter; the far end of the catheter is provided with a hose part including a main elastic spring ring inside, and the farthest end of the catheter is combined with a probe provided with a shooting module and luminophors inside; two pull wires are arranged in the catheter; and the near ends of the two pull wires are extended and are combined on the control mechanism, and the far ends of the two pull wires are respectively arranged in two small elastic spring rings in a penetration manner and are fixed. The probe can be stably combined with the shooting module and the luminophors, so the shooting stability is improved.

8 Claims, 7 Drawing Sheets

(56) References Cited

U.S. PATENT DOCUMENTS

2006/0157059 A1* 7/2006 Johnson ................ A61M 16/04
                                                    128/207.14
2011/0162643 A1* 7/2011 Aita ...................... A61B 1/267
                                                    128/200.26

* cited by examiner

TRACHEOSCOPE

CROSS REFERENCE TO RELATED APPLICATIONS

The present application claims the benefit of Taiwanese Patent Application Nos. 106201408 and 106102871 filed on Jan. 25, 2017. All the above are hereby incorporated by reference.

TECHNICAL FIELD

The invention is an innovative design of a tracheoscope and mainly provides a skillful and stable combined structure which can effectively control swinging, bending and positioning effects of the far end of a catheter of the tracheoscope and improves the combined stability of a shooting module and luminophors in a probe by means of a simpler operation manner, and simultaneously has the practicability.

BACKGROUND

At present, a tracheoscope structure generally includes a handle provided with a control mechanism. One end of the handle is combined with an elongated catheter so as to extend into a human body. The far end of the catheter is combined with a probe including a shooting module inside, so as to shoot an image in a human body cavity and send the image to an external screen, and therefore a medical staff observes or gives treatment directly. In order to get images at different angular positions inside the human body, a hose part that may be bent is arranged at the far end of the catheter. Two pull wires are operated using the control mechanism so as to control the hose to swing and link the probe to rotate, thereby obtaining multiple intracavitary images at different angles.

People know that such tracheoscope includes the control mechanism, and the design of a bending structure of the hose part and the structure of the probe at the far end are different. However, all are not up to the convenience and the practicability in use. For example, for a well-known bending control structure, when the far end of the catheter is bent to be positioned, it must be implemented in an artificial manner. By buckling a fixed position with a hand power, the positioning of the bending angle of the catheter is guaranteed. But there still has a problem on a displacement. Alternatively, a lock mechanism is provided and there is a need to press a clamping mechanism again to lock a button. When the angle at the far end of the catheter is required to be changed, a second hand is used additionally to unlock, which inevitably causes the convenience and trouble in use and is very difficult to meet the requirements of a single-hand operation. Additionally, for a well-known structure in which the hose at the far end of the catheter is bent, it is a commonplace that multiple units are combined to form a swingable supporting body held in the hose part. However, for such a structure, the manufacturing is time-consuming, the machining is very troublesome, the combination to control the bending of the hose is not necessarily smooth, and once some unit breaks down, whole structure cannot be used, all of which are not practical. Regarding that the probe at the far end is combined with components such as the shooting module and the luminophors inside and a moulding manner of a reserved working channel, the common practice is to use a mould and first place each component first. Since there is no a length structure for positioning at the outlet end, it is frequent to occur a phenomenon that the shooting module, the luminophors or the working channel are out of position due to each internal component lacks an effective positioning design during glue filling and encapsulation. As a result, a product has a flaw or a fault, which is not beneficial to the accurate operation. Moreover, the glue solidifying time is overlong. Therefore, it is necessary to improve the existing known tracheoscope design.

SUMMARY

The invention discloses a tracheoscope and mainly provides a novel tracheoscope that can simply control the movement of two pull wires inside a catheter of the tracheoscope, links a hose part at a far end of the catheter to swing and bend, and can locate its angle in a simple and easy way The objectives of the invention are implemented by the following technical solutions.

A tracheoscope includes a handle combined with a control mechanism; one end of the handle is connected with a plug-in type screen, and the other end of the handle is combined with a catheter; the far end of the catheter is provided with a hose part having a main elastic spring ring inside, and the farthest end of the catheter is further combined with a probe provided with a shooting module and luminophors inside; two pull wires are arranged in the catheter; the near ends of the two pull wires are extended and are combined on the control mechanism, and the far ends of the two pull wires are respectively arranged in two small elastic spring rings in a penetration manner and are fixed. By pressing a control piece above the handle, the two pull wires are operated and are linked in a manner of moving back and forth so as to change relative positions of the two pull wires, thereby achieving the objective that the hose part and the probe at the external end of the catheter are bent toward different directions. Moreover, the probe at the far end of the catheter can be positioned at the angle.

In addition, the hose part can be bent smoothly and laterally under the cooperation of the main elastic spring ring and the two small elastic spring rings, and the probe can be stably and accurately combined with components such as the shooting module and the luminophors. That is, the improved tracheoscope provided by the invention has significant progresses of simple operation, shooting stability and the like.

BRIEF DESCRIPTION OF THE DRAWINGS

FIG. 3 is pressed.

Figure 1:
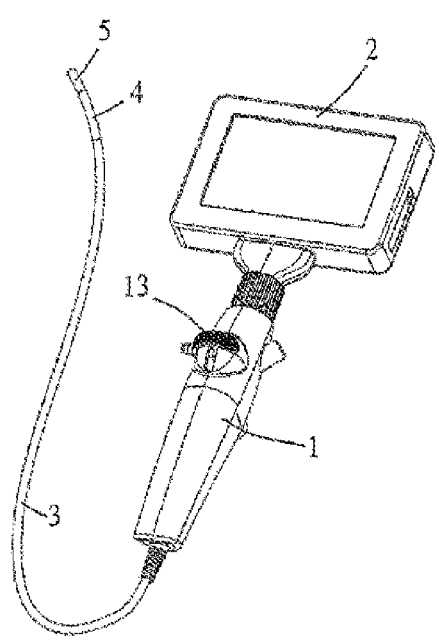
FIG. 1 is an external stereoscopic diagram of a tracheoscope of the invention.

Reference numbers in the drawings are set forth hereinafter:

1 a handle; 2 a plug-in type screen; 3 a catheter; 4 a hose part; 5 a probe; 6 a spherical body; 7 a rotating wheel; 8 a holding groove; 9 a spring; 10 a brake block; 11 a non-slip piece; 12 a long slotted hole; 13 a control piece; 14 a connection rod; 15 a central hole; 16 a pull wire; 17 a small elastic spring ring; 18 a fixed seat; 20 a main spring elastic ring; 21 a central vertical plate; 22 a penetration hole; 23 a positioning plate; 24 a central opening; 25 an elastic strip; 26 a hollow external pipe; 27 an end panel; 28 an apparatus hole; 29 a camera lens hole; 30 a light hole; 31 a clamping seat; 32 an apparatus pipe; 33 a shooting module; 34 a camera lens; 35 a step-like groove; 36 a waterproof lenses; 37 a luminophor

DETAILED DESCRIPTION OF THE EMBODIMENTS

Figure 2:
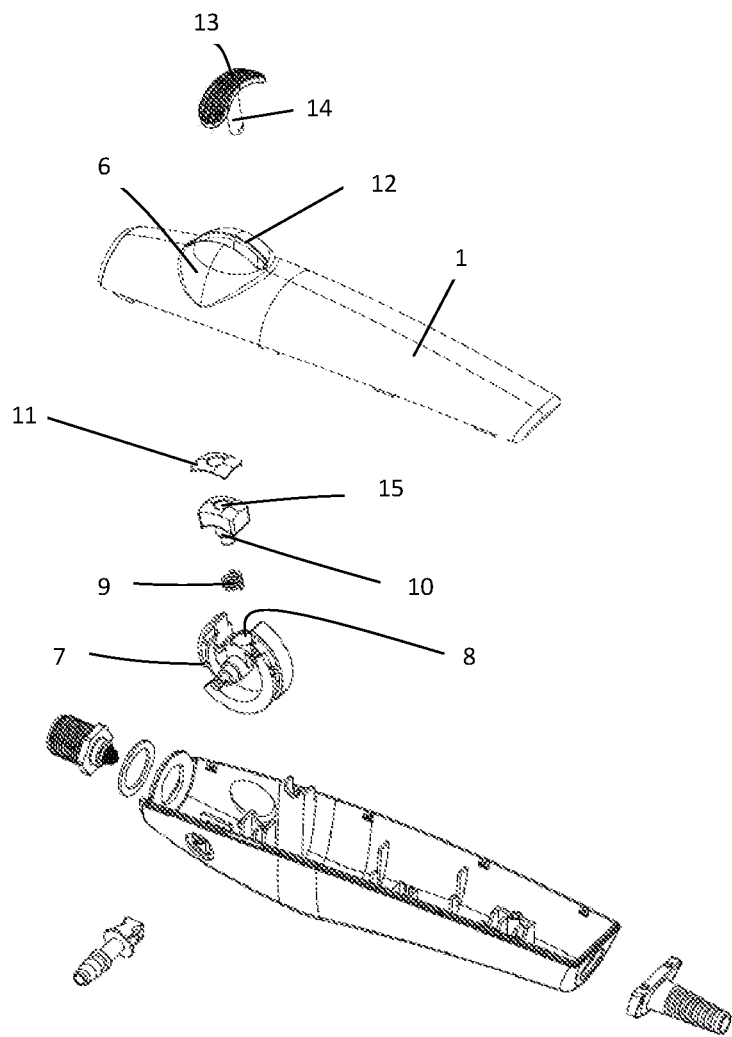
FIG. 2 is a breakdown stereoscopic diagram of a handle and a control mechanism of a tracheoscope of the invention.
Figure 3:
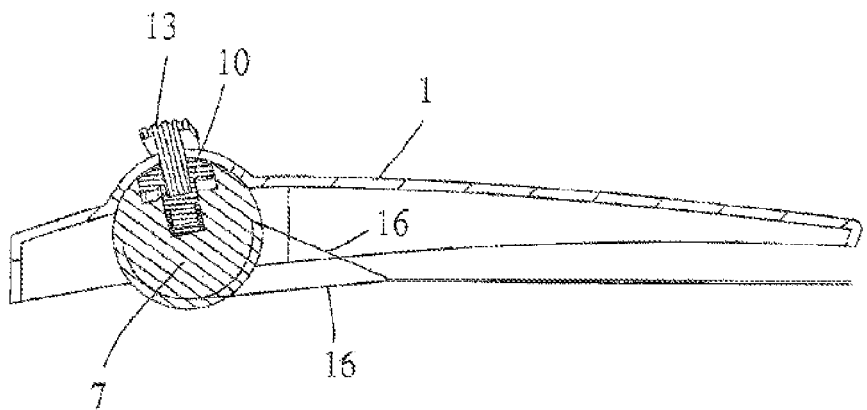
FIG. 3 is a combined cross-section diagram of FIG. 2 of the invention.
Figure 4:
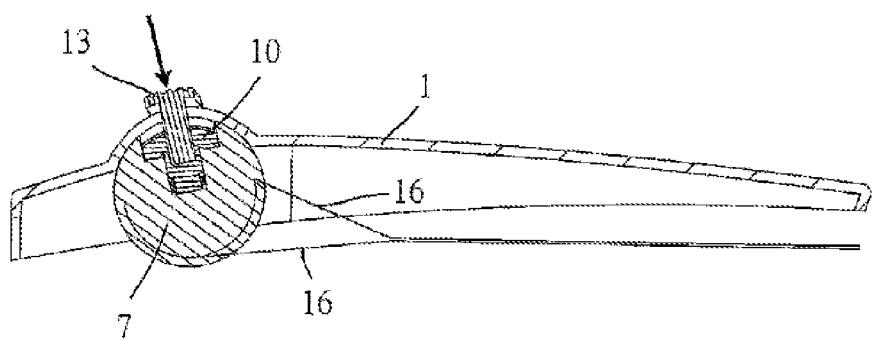
FIG. 4 is a cross-section diagram of the invention after
Figure 5:
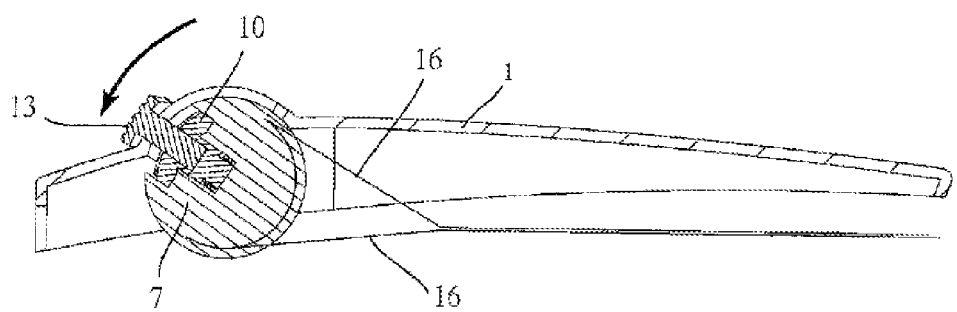
FIG. 5 and FIG. 6 are diagrams of an embodiment of the invention in which a control piece is moved back and forth as shown in FIG. 4.
Figure 6:
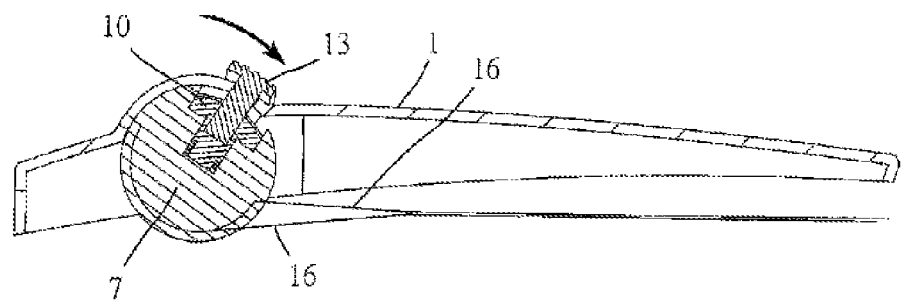

Please referring to FIG. 1-3 first, the embodiment is an improved design of a tracheoscope, including a handle 1; one end of the handle 1 is connected with a plug-in type screen 2, and the other end of the handle 1 is combined with a catheter 3; the far end of the catheter 3 is a hose part 4, and the farthest end of the catheter 3 is combined with a probe 5, wherein a control mechanism is provided inside the handle 1; the control mechanism includes a rotating wheel 7; the rotating wheel 7 is pivotally arranged inside the handle 1 to form a rotatable structure; a holding groove 8 is formed on an upper portion of the rotating wheel 7; a spring 9 and a brake block 10 are arranged in the groove; an upper portion of the brake block 10 is of an arc shape and is combined with an arc non-slip piece 11; the handle 1 is provided with a spherical body 6 relative to an upper portion position of the rotating wheel 7, and is provided with a longitudinal long slotted hole 12; the control mechanism additionally includes a control piece 13; a connection rod 14 is arranged below the control piece 13; the control piece 13 is arranged above the spherical body 6 of the handle 1; the connection rod 14 below the control piece 13 passes through the long slotted hole 12 and is combined with a central hole 15 of the brake piece 10 of the control mechanism inside; and thus, through the movement of the control piece 13, the brake block 10 is controlled to drive the rotating wheel 7 to rotate.

Figure 9:
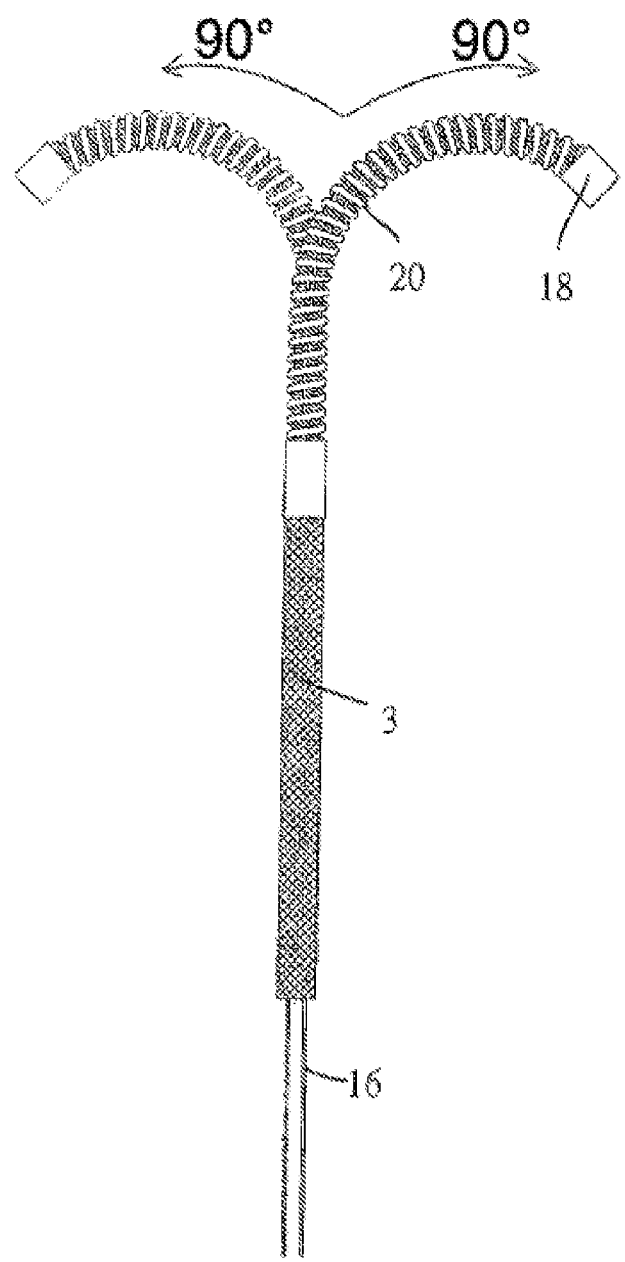
FIG. 9 is a systematic diagram for bending a far end of a catheter of a tracheoscope of the invention.

Two pull wires 16 are arranged inside the catheter 3 of the tracheoscope; the near ends of the two pull wires 16 are extended and are combined on the rotating wheel 7 of the control mechanism, and the far ends of the two pull wires 16 are respectively arranged in two small elastic spring rings 17 in a penetration manner and are combined with a fixed seat 18 at the far end; the catheter 3 is provided with the hose part 4 at the far end, and a main elastic spring ring 20, the two small elastic spring rings 17 and the fixed seat 18 inside. Please referring to FIG. 4-8, the main elastic spring ring 20 is arranged inside the hose part 4 at the far end of the catheter 3 of the tracheoscope; the two small elastic spring rings 17 are arranged at the internal opposite two sides of the main elastic spring ring 20 such that the two pull wires 16 of the tracheoscope are respectively penetrated therebetween; the foregoing fixed seat 18 is held at the farthest end of the hose part 4, and is provided with a central vertical plate 21 as well as multiple penetration holes 22 at the two sides; the far ends of the two pull wires 16 are respectively penetrated through the penetration holes 22 at the two sides of the fixed seat 18 and are fixed by a positioning plate 23. Therefore, by applying a force to different pull wires 16, the fixed seat 18 can be linked to swing to different lateral directions as shown in FIG. 9, thereby achieving the purpose of controlling a state that the hose part 4 can be laterally swung such that the far end of the catheter 3 is bent. Please referring to FIG. 10 again, it is a changed embodiment of the invention, wherein a structure of the fixed seat 18 is provided with a central opening 24, and is provided with a plurality of the penetration holes 22 on an annular external portion; the central opening 24 can be used for connecting an appliance pipe 32, such that a hollow inside is formed into a working channel; the far ends of the two pull wires 16 are also respectively arranged in the two penetration holes 22 at opposite sides of the fixed seat 18 in a penetration manner; an elastic strip 25 is arranged in each of the two penetration holes 22 at the other two perpendicular sides of the two pull wires 16; the fixed seat 16 can be bent accurately toward a corresponding direction under the linkage of the different pull wires 16, and the hose part 4 at the far end of the catheter 3 is bent and swung toward the same direction. Hence, the invention can make the catheter 3 be applied to the tracheoscope having a working pipeline, and the practicability and the progressiveness are improved.

Figure 11:
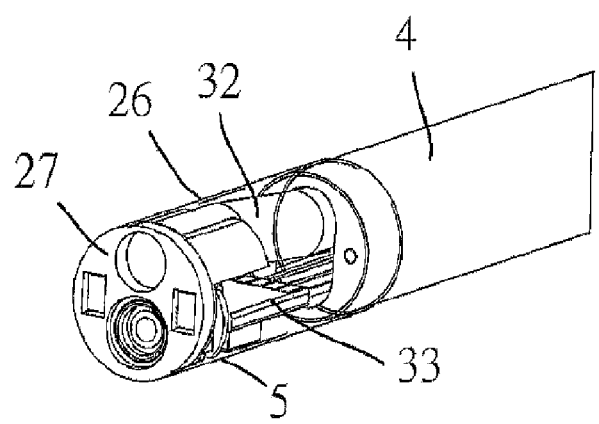
FIG. 11 is a perspective stereoscopic diagram of a probe structure of a tracheoscope of the invention.
Figure 12:
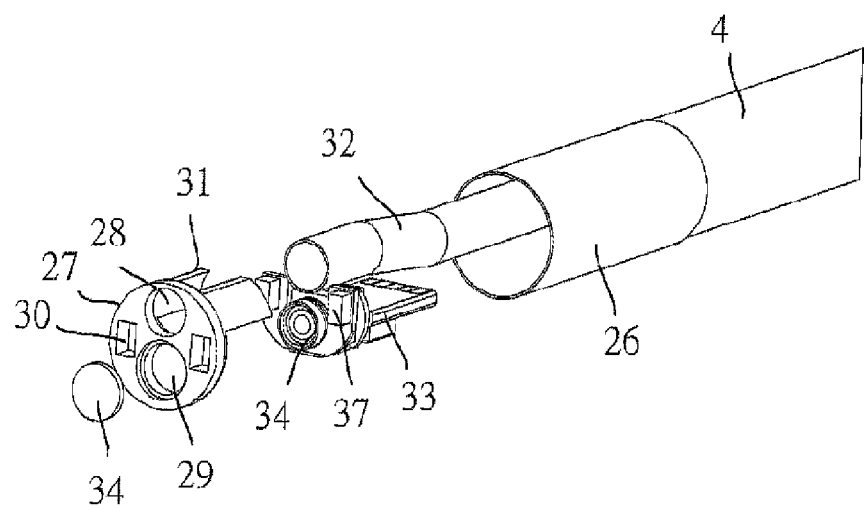
FIG. 12 is a breakdown diagram of the invention as shown in FIG. 11.

In the embodiment, the probe 5 is combined at the farthest end of the catheter 3 of the tracheoscope, and includes a hollow external pipe 26 and an end panel 27. As shown in FIG. 11 and FIG. 12, the end panel 27 is combined at the external end of the hollow external pipe 26; an appliance hole 28, a camera lens hole 29 and two light holes 30 are formed on the end panel 27; two clamping seats 31 are arranged inside the end panel 27 and at the lateral edge of the appliance hole 28; in assemble, the far end of the appliance pipe 32 taken as the working channel is buckled on the appliance hole 28 and is stably clamped by the two clamping seats 31; a camera lens 34 of the shooting module 33 is clamped at the camera lens hole 29; additionally, a step-like groove 35 is formed at the front edge of the camera lens hole 29, such that a waterproof lens 36 is combined outside the camera lens 34. Moreover, the luminophors 37 positioned at the two sides of the front end of the shooting module 33 are clamped into the opposite light holes 30 of the end panel 27, such that each of the components reaches to a stable combined state. Then by performing the glue filling and encapsulating procedures in front and back of the hollow external pipe 1, the perfect structure of the probe 5 at the far end is achieved, and all components including the shooting module 33 and the luminophors 37 inside can be positioned at preset positions and cannot be shifted. At last, the hose part 4 at the far end of the catheter 3 of the tracheoscope is combined with the near end of the hollow external pipe 26 in a waterproof manner, thereby forming an innovative combined structure of the invention.

Figure 7:
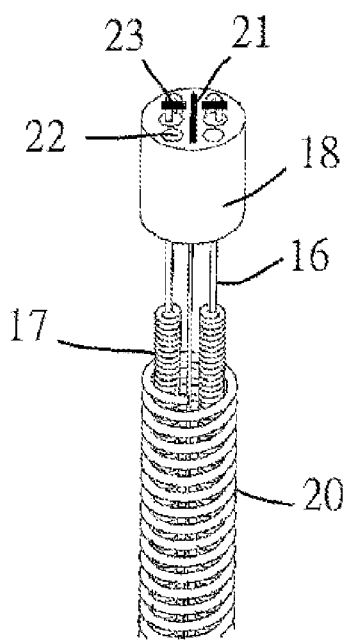
FIG. 7 is a stereoscopic diagram of an internal structure of a hose part of a tracheoscope of the invention.
Figure 8:
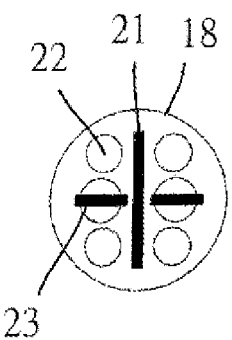
FIG. 8 is a top plane diagram of the FIG. 7.
Figure 10:
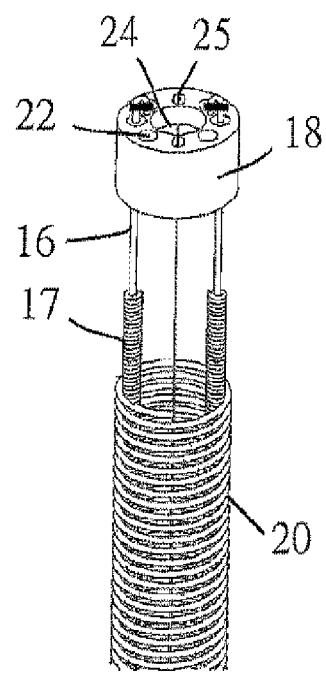
FIG. 10 is a stereoscopic diagram of another application example of a fixed seat of the invention.

When the tracheoscope is applied, an operator can simply press the control piece 13, such that the brake block 10 downwardly compresses the spring 9, and the non-slip piece 11 leaves away from the inner surface of the spherical body 6. As shown in FIG. 10, the control piece 13 can be operated easily to move back and forth so as to drive the rotating wheel 7 to rotate forwardly and reversely, thereby achieving the purpose of controlling positions of the linked two pull wires 16 and thus enabling the far end of the catheter 3 to bend toward different directions. As shown in FIG. 11, FIG. 12 and FIG. 7, with such an operating manner, the operator can implement easily only with a single hand without distraction. When the far end of the catheter 3 is bent to a certain special angle, as long as the pressing finger is released, the spring 9 pushes the brake block 10 upward by a restoring force and the non-slip piece 11 is tightly attached to the inner surface of the spherical body 6 of the handle. For a position as shown in FIG. 3, the positioning effect like a brake is obtained. When the rotating wheel 7 is fixed at this position, the far end of the catheter 3 and the probe 5 are positioned at the bending angle, thereby stably shooting to obtain an image at this position and retransmitting image data to the plug-in type screen 2 at the other end of the handle 1 via an internal line. Furthermore, the operator can clearly observe the image without spending a mind and a power for maintenance and can give the medical treatment wholeheartedly, achieving the progressiveness and the practicability of the invention. In addition, in the invention, an external large screen can be used to replace the plug-in screen 2 so as to amply a shot image to obtain a better judgment effect.

In conclusion, through the improved tracheoscope of the invention, the operator can control the far end of the catheter of the tracheoscope to bend and the probe to swing simply with the single hand and may easily fix the probe at the selected bending angle and position, thereby providing a stable image to observe directly by the screen at the other end of the handle. With the shooting module, the luminophors, or even the working channel, the accurate and stable combination can be guaranteed. That is, the effects achieved by the invention have better progressiveness and practicability than the well-known design.

What is claimed is:

1. A tracheoscope, comprising a handle, one end of the handle being connected with a plug-in type screen or an external large screen, and the other end of the handle being combined with a catheter, the far end of the catheter being provided with a hose part and the end of the hose part being combined with a probe, the tracheoscope being characterized in that:
    a control mechanism is arranged inside the handle and comprises:
    a rotating wheel, which is pivotally arranged inside the handle to form a rotatable structure, a holding groove being formed on an upper portion of the rotating wheel;
    a brake block, which is arranged in the holding groove of a rotating shaft, provided with a spring thereunder, an upper portion of the brake block being arranged into an arc shape, the upper portion of the brake block is provided with a central hole, and being additionally combined with a non-slip piece;
    the handle being arranged into a spherical body structure relative to an upper portion position of the rotating wheel and being provided with a longitudinal long slotted hole;
    a control piece, which is arranged above a spherical body of the handle and is provided with a connection rod thereunder, the connection rod being penetrated through the long slotted hole on the spherical body and being combined with the central hole on the brake piece thereunder;
    two pull wires are arranged inside the catheter of the tracheoscope, and the near ends of the two pull wires of the tracheoscope are extended and are combined on the rotating shaft of the control mechanism;
    a main elastic spring ring, two small elastic spring rings and a fixed seat are arranged inside the hose part, wherein
    the main elastic spring ring is arranged in the hose part and the outer diameter of the main elastic spring ring is smaller than the inner diameter of the hose part;
    the two small elastic spring rings are arranged at the internal opposite two sides of the main elastic spring;
    the two pull wires are respectively penetrated through the two small elastic spring rings;
    the fixed seat is combined at the farthest end of the hose part and is provided with multiple penetration holes; the far ends of the two pull wires are respectively penetrated through two penetration holes and are respectively combined to be fixed by a positioning plate; and
    the probe comprises:
    a hollow external pipe;
    an end panel, which is combined at the external end of the hollow external pipe, is provided with an appliance hole, a camera lens hole and light holes, and is provided with a clamping seat at a lateral edge inside the appliance hole;
    an appliance pipe, whose external end is buckled to the appliance hole and which is clamped by the clamping seat; and
    a shooting module, which is provided with a camera lens and multiple luminophors, the camera lens being combined at the camera lens hole, and the luminophors being positioned at the two sides of the front end of the shooting module and being also clamped into the light holes of the end panel.

2. The tracheoscope as claimed in claim 1, wherein when the control piece is pressed such that the tracheoscope is moved back and forth, the brake block is linked, thereby driving the rotating wheel to rotate and change positions of the pull wires and thus enabling a hose at the far end of the catheter of the tracheoscope to generate a bending angle with the probe.

3. The tracheoscope as claimed in claim 1, wherein when the control piece is not pressed, the non-slip piece on the brake piece is tightly attached to an inner surface of the spherical body of the handle via an upward elastic force of the spring, such that the rotating wheel, the pull wires, and the probe at the far end of the catheter all are positioned in a stable positioned state.

4. The tracheoscope as claimed in claim 1, wherein the fixed seat is provided with a central vertical plate; the penetration holes are formed at the two sides of the central vertical plate, such that the far ends of the two pull wires are respectively penetrated through middle penetration holes at the two sides of the central vertical plate of the fixed seat.

5. The tracheoscope as claimed in claim 1, wherein a central opening is formed on the fixed seat and can be combined with an appliance pipe to form a working channel; each of the penetration hole is formed on an annular portion at the external edge of the fixed seat; a directing strip is respectively arranged in the penetration holes at the opposite two sides; the far ends of the two pull wires are respectively penetrated through the two penetration holes at the other two sides of the fixed seat.

6. The tracheoscope as claimed in claim 1, wherein the fixed seat can be swung to a corresponding direction accurately via movements of different pull wires; and the hose part at the far end of the catheter is linked to bend and rotate to the same direction.

7. The tracheoscope as claimed in claim 1, wherein a step-like groove is formed at the front edge of the camera lens hole of the end panel, so as to combine with a waterproof lens.

8. The tracheoscope as claimed in claim 1, wherein the near end of the hollow external pipe and the far end of the catheter of the tracheoscope are combined in a waterproof manner.

\* \* \* \* \*